United States Patent
Singh et al.

(10) Patent No.: US 6,511,821 B2
(45) Date of Patent: Jan. 28, 2003

(54) PROCESS FOR THE PREPARATION OF NOVEL GROWTH MEDIA FROM DISTILLATION AND OTHER PLANT WASTES FOR MASS MULTIPLICATION OF BIO-CONTROL FUNGI

(75) Inventors: Harikesh Bahadur Singh; Alok Kalra; Nirmal Kumar Patra; Sushil Kumar; Rakesh Pandey; Suman Preet Singh Khanuja; Ajit Kumar Shasany, all of Lucknow (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/810,494

(22) Filed: Mar. 19, 2001

(65) Prior Publication Data

US 2002/0028500 A1 Mar. 7, 2002

Related U.S. Application Data

(63) Continuation-in-part of application No. 09/281,784, filed on Mar. 31, 1999.

(30) Foreign Application Priority Data

Dec. 2, 1999 (IN) .................................................. 235/99

(51) Int. Cl.[7] .................................................. C12P 39/00
(52) U.S. Cl. ...................... 435/42; 435/256.8; 435/911; 435/945
(58) Field of Search ................................ 435/42, 256.8, 435/945, 911

(56) References Cited

PUBLICATIONS

Biological Control of Soil–Borne Plant Pathogens by Trichoderma Spp., A.N. Mukhopadhyay, Presidential Address Delivered at Annual Conference of Society of Mycology and Plant Pathology on Jan. 15, 1987, *Indian J. Mycol & Pl. Pathol.*, vol. 17, pp. 1–10, (1987).

Effect of Peat–Bran Inoculum of Trichoderma Species on Biological Control of *Rhizoctonia solani* in Lettuce, P.A. Maplestone et al., *Plant and Soil*, vol. 136:257–263, (1991).

Mass Multiplication of Trichoderma Spp., Kousalya Gangadharan et al., *J. Biol. Control*, 4 (1), pp. 70–71 (1990).

Residue Recycling for Restoring Soil Fertility and Productivity in Japanese Mint (*Mentha Arvensis*) Mustard (*Brassica Sp.*) System, D.D. Patra et al., T. Ando et al. (Eds.) *Plant Nutrition—for Sustainable Food Production And Environment*, 587–588 (1997).

A Simple Method for Achieving High CFU of *Trichoderma harzianum* on Organic Wastes for Field Applications, Indu S. Sawant et al., *Indian Phytopathology*, 49(2): 185–187 (1996).

*Primary Examiner*—Herbert J. Lilling
(74) *Attorney, Agent, or Firm*—Fitzpatrick, Cella, Harper & Scinto

(57) ABSTRACT

A process for the preparation of a growth media for mass multiplication of bio-control fungi, comprising a chopped, shade-dried distillation waste in a plastic bag that is plugged with cotton followed by autoclaving and an inoculation of a strain of bio-control fungi such as *Trichoderma harzianum* or *Gliocladium virens*, and incubating the bags at room temperature for 14–30 days, and then shade drying and grinding the product to obtain a fine powder.

5 Claims, 1 Drawing Sheet

PROCESS FOR THE PREPARATION OF NOVEL GROWTH MEDIA FROM DISTILLATION AND OTHER PLANT WASTES FOR MASS MULTIPLICATION OF BIO-CONTROL FUNGI

CROSS-REFERENCE TO RELATED APPLICATIONS

This is a Continuation-in-Part of application Ser. No. 09/281,784, filed Mar. 31, 1999.

FIELD OF THE INVENTION

This invention relates to a process for the preparation of novel growth media from distillation and other medicinal plant wastes for mass multiplication of bio-control fungi.

BACKGROUND

Experiments have been carried out and a new process has been developed for the large scale production of a cheap growth media from distillation and other medicinal plant wastes for the multiplication of two well known bio-control fungi viz. *Trichoderma harzianum* Ri (ATCC 66869) and *Gliocladium vivirde* Matru (ATCC 32912) for the control of plant diseases. A particular strain of *Trichoderma harzianum* TH (ATCC PTA-3701) was redeposited with the American Type Culture Collection, Manassas, Va. 20110-2209, on behalf of CIMAP on Sep. 11, 2001, (to replace a specimen originally submitted on Nov. 20, 2000 which failed a viability test) and a particular strain of *Gliocladium virens=trichoderma virens* GV (ATCC PTA-2710), deposited with the American Type Culture Collection, Manassas, Va. 20110-2209, on behalf of CIMAP on Nov. 20, 2000, are preferred embodiments of the present disclosure.

Although there are a large number of growth media found suitable for these fungi, most of these, besides being drawn from the useful food grains like wheat, sorghum, maize etc., are generally expensive. In an experiment conducted to screen different growth media for mass culture of Trichoderma and Gliocladium, it has been observed that the distillation waste of two essential oil crops viz. Citronella (*Cymbopogon winterianus*) and Japanese mint (*Mentha arvensis*) can be successfully utilized for the production of mass inoculum of these two fungi. Similarly, the non-utilized parts of medicinal plants like poppy capsule shell and musk dana fruits etc. have been found suitable for the purpose.

Biological disease control is a promising strategy for managing soil borne or foliar pathogens in a wide range of crops. In recent years, because of difficulties in controlling the soil borne plant pathogens by conventional chemical methods, there have been many attempts at biological disease control especially with the species of Trichoderma and Gliocladium. One of the most critical obstacles to biological disease control by direct massive soil augmentation has been the lack or scarcity of methods of mass culturing for delivering antagonists to the soil. For this, various formulations have been tested. These include:

(a) fermentor biomass in pulverized pyrophylite or in alginate pellets,
(b) wheat or rice bran inocula,
(c) inoculum multiplied on seeds/grains of various cereals and millets and
(d) many other formulations utilizing inorganic salts and other organic substances.

(Mukhopadhyay, 1987 *Indian J Mycol and Pl. Path*. 17: 1–9; Maplestone et al., 1991 *Plant and Soil*, 136: 257–263).

The distilled waste of various aromatic crops and the non-utilized parts of medicinal and other plants are of limited economic use. Distillation waste retains the nutritional value and hence, can be recycled to the crop as potential source for supplementing the nutritional requirement of subsequent crop. This waste obtained as a by-product in hydro-distillation of fresh herbage is a potential source of nitrogen and other nutrients. Though some agricultural by-products and agricultural wastes have been tested for mass culturing of Trichoderma and Gliocladium (Gangadharan and Jeyarajan, 1990 *J. Biol. Control*. 470–71, Sawant and Sawant, 1996, *Indian Phytopath* 49: 185–187), no information so far exists on the possibility of using distillation waste as growth medium of these fungi.

OBJECTS OF THE INVENTION

The object of the present invention is to develop an improved process for the production of a growth media for mass production of bio-control fungi which obviates the drawbacks of the existing methods.

Another object of the present invention is to develop a cheap growth media for the multiplication of well known bio-control fungi viz. *Trichoderma harzianum* TH, *Trichoderma harzianum* Ri, *Gliocladium virens* GV and *Gliocladium viride* Matru where distillation wastes of some aromatic crops like citronella, mints, lemongrass etc., and the non-uilised parts of medicinal plants like poppy capsule husk and musk dana fruits etc., can be used.

SUMMARY OF THE INVENTION

To meet the above objects, a present invention provides a process for the preparation of a growth media for mass multiplication of bio-control fungi, which comprises (a) shade drying of distillation waste recovered after distillation of plant herbage, (b) chopping this shade dried distillation waste, (c) filling the distillation waste in poly-propylene or poly-ethylene bags, (d) plugging the said bags with cotton followed by autoclaving at 15 lbs pressure for one hour and inoculation of these bags with any of *Trichoderma harzianum* TH (ATCC PTA-1920); *Trichoderma harzianum* Ri (ATCC No. 6089), *Gliocladium virens* GV (ATCC PTA-2710) and *Gliocladium viride Matru (ATCC No.* 32912), (e) incubation of the bags in well illuminated room at room temperature ranging between 15–34° C. for 14–30 days and (f) shade drying of the resultant product and grinding the same in a blender to obtain a fine powder.

DETAILED DESCRIPTION OF THE INVENTION

This invention relates to a improved process for the preparation of novel growth media from distillation wastes for mass multiplication of bio-control fungi viz. *Trichoderma harzianum* TH; *Trichoderma harzianum* Ri, *Gliocladium virens* GV and *Gliocladium viride Matru*. The growth media are preferably the distillation waste of *Cymbopogon winterianus* and *Mentha arvensis*. In these, waste maximum growth of the above said bio-control fungi was observed, not reported earlier.

Figure 1:
FIG. 1 shows inoculated bag with *Trichoderma harzianum* TH (ATCC No. PTA-3701)
Figure 2:
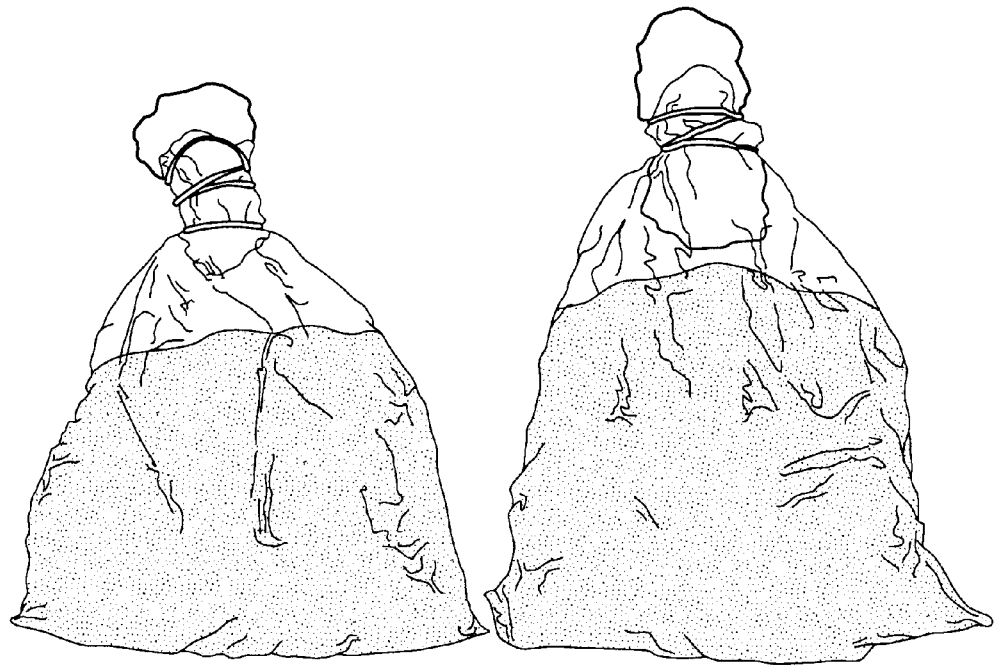
FIG. 2 shows inoculated bag with *Gliocladium virens* GV (ATCC No. PTA-2710)

According, the present invention provides an improved process for the preparation of a growth media for mass multiplication of bio-control fungi which comprises (a) shade drying of distillation waste recovered after distillation of plant herbage (b) chopping this shade dried distillation waste (c) filling the distillation waste in poly-propylene or polyethylene bags (d) plugging the said bags with cotton followed by autoclaving at 15 lbs pressure for one hour and inoculation of these bags with *Trichoderma harzianum* TH (ATCC No. PTA-3701) as shown in FIG. 1 and *Gliocladium virens* GV (ATCC No. PTA-2710) as shown in FIG. 2 (e) incubation of the bags in well illuminated room at room temperature ranging between 15–34° C. for 14–30 days (f) shade drying of the resultant product and grinding the same in a blender to obtain a fine powder.

In an embodiment of the invention, the distillation waste used may be selected from aromatic plants from the group consisting of citronella (*Cymbopogon winterianus*) mints (Mentha sp), palmarosa (*Cymbopogon martinii*) or unused waste of poppy husk shell and musk dana fruit.

In a preferred embodiment, the distillation waste used may be selected from *Cymbopogon winterianus* and *Mentha arvensis*.

In another embodiment of the invention, the filling of the wastes may be carried out in poly-propylene/poly-ethylene, synthetic, semi-synthetic, natural bags and containers resistant to water and distillation wastes.

In yet another embodiment of the invention, the bio-control fungi may be selected from *Trichoderma harzianum* TH; *Trichoderma harzianum* Ri, *Gliocladium viride Matru*, *Trichoderma virens*, etc., or micro-organisms that can grow in distillation wastes.

The invention is described in detail in the examples given below which are provided to illustrate the invention and therefore should not be construed to limit the scope of the present invention.

EXAMPLE 1

Moistened shade dried distilled waste (500 g) of various aromatic crops (*Cymbopogon winterianus, C. martinii, C. flexuosus, Mentha arvensis, M. spicata, M. piperita*) was filled in 25×35 cm PP bags. The bags were plugged with cotton and autoclaved at 15 lbs pressure for one hour. These bags along with the bags containing seven most common conventional media were inoculated by injecting 5 ml of spore suspension of *T. harzianum* TH and *G. virens* GV by hypodermic syringe bags were incubated in well-illuminated room at room temperature (25–32 ° C. ) for 20 days after which colony forming units (cfu) were estimated. Of the seven most common media tested for mass multiplication of Trichoderma and Gliocladium, the sorghum grain medium revealed the maximum growth (as expressed by cfu) of the fungi. However, the growth of both the fungi was further high when grown on distillation waste of *Cymbopogon winterianus* and *Mentha arvensis* (Table 1).

TABLE 1

Effect of medium on the growth of *Trichoderma harzianum* TH and *Gliocladium virens* GV

| Medium | Colony forming units (cfu) recovered in the cultures of | |
|---|---|---|
| | *Trichoderma harzianum* ($\times 10^7$) | *Gliocladium viride* ($\times 10^8$) |
| Conventional media based on | | |
| a) Sorghum grain | 2.4 | 5.5 |
| b) Wheat bran | 2.0 | 7.8 |
| c) Maize meal | 2.0 | 6.5 |
| d) Wheat bran-saw dust | 1.3 | 1.9 |
| e) Bajra grain | 1.2 | 2.3 |
| f) Rice bran | 0.7 | 2.8 |
| Media based on distilled herbage | | |
| g) Citronella (*Cymbopogon winterianus*) | 4.2 | 16.1 |
| h) Menthol mint (*Mentha arvensis*) | 3.8 | 15.0 |
| I) Palmarosa (*Cymbopogon martinii*) | 2.7 | 5.8 |
| j) Lemon grass (*C. flexuosus*) | 1.5 | 5.0 |
| k) Spearmint (*M. spicata*) | 1.1 | 6.1 |
| l) Peppermint (*M. pipenta*) | 0.7 | 3.8 |

Further, experiments were conducted using poppy capsule shell and musk dana fruit and growth of the above said fungi was observed in those waste.

EXAMPLE 2

The earthen pots (9" dia ) were filled with sterilized soil (clayey loam in texture, pH 7.4) and inoculated (@ 5g/kg soil) with the bio-control fungi grown on wheat bran and sorghum grain media (selected on the basis of higher cfu obtained in Example 1) and distilled wastes of *M. arvensis* and *C. winterianus* (found superior out of 6 tested in Example 1). Colony forming units (cfu) of both *T. harzianum* TH and *G. virens* GV recovered from the soil after 10–50 days of inoculation were higher in soil samples supplemented with distilled herbage of *C. winterianus* and *M. arvensis* (Table 2).

TABLE 2

Colony forming Unit (cfu) of *Trichoderma harzianum* TH and *Gliocladium virens* GV recovered from soil supplemented with different media

| Multiplication medium | cfu of fungi recovered after varying incubation periods (days) | | | | | | | | | |
|---|---|---|---|---|---|---|---|---|---|---|
| | *Trichoderma harzianum* | | | | | *Gliocladium viride* | | | | |
| | 10 | 20 | 30 | 40 | 50 | 10 | 20 | 30 | 40 | 50 |
| Wheat bran | $7.2 \times 10^8$ | $2.4 \times 10^7$ | $9.0 \times 10^6$ | $8.0 \times 10^5$ | $4.6 \times 10^4$ | $9.2 \times 10^9$ | $4.6 \times 10^8$ | $4.6 \times 10^7$ | $3.2 \times 10^6$ | $2.1 \times 10^5$ |
| Sorghum grain | $6.1 \times 10^8$ | $2.0 \times 10^7$ | $1.5 \times 10^6$ | $8.4 \times 10^5$ | $3.6 \times 10^4$ | $8.8 \times 10^9$ | $7.6 \times 10^8$ | $8.4 \times 10^7$ | $4.9 \times 10^6$ | $3.7 \times 10^5$ |
| *Mentha arvensis* distilled herbage | $6.6 \times 10^9$ | $4.6 \times 10^8$ | $3.0 \times 10^7$ | $3.6 \times 10^6$ | $1.5 \times 10^5$ | $1.8 \times 10^{10}$ | $2.8 \times 10^9$ | $1.7 \times 10^8$ | $2.1 \times 10^7$ | $2.6 \times 10^6$ |

TABLE 2-continued

Colony forming Unit (cfu) of *Trichoderma harzianum* TH and *Gliocladium virens* GV recovered from soil supplemented with different media

| Multiplication medium | cfu of fungi recovered after varying incubation periods (days) | | | | | | | | | |
|---|---|---|---|---|---|---|---|---|---|---|
| | *Trichoderma harzianum* | | | | | *Gliocladium viride* | | | | |
| | 10 | 20 | 30 | 40 | 50 | 10 | 20 | 30 | 40 | 50 |
| *Cymbopogon winterianus* distilled herbage | $9.2 \times 10^9$ | $6.6 \times 10^8$ | $3.4 \times 10^7$ | $5.5 \times 10^6$ | $1.8 \times 10^5$ | $2.3 \times 10^{10}$ | $3.8 \times 10^9$ | $3.1 \times 10^8$ | $2.6 \times 10^7$ | $2.4 \times 10^6$ |

EXAMPLE 3

Survival of *T. harzianum* TH and *G. virens* GV on storage of their culture mass was tested on both conventional media and media based on distilled herbage (as in Example 2). The cultures were stored in PP bags at room temperature (20–36° C.) for 6 months. Survival of the fungi was found to be higher in case where these fungi were grown on distilled wastes (Table 3).

EXAMPLE 4

Collar rot and wilt caused by *Sclerotium rolfsii* is a destructive disease of *M. arvensis*. A good protection of *M. arvensis* plants from collar rot and wilt could be achieved with the application of bio-control fungi grown on *C. winterianus* (Table 4) in *S. rolfsii* infested earthen pots and was at par with protection afforded by conventional growth media (Sorghum grain).

TABLE 4

Protection provided by soil application of *Trichoderma harzianum* TH and *Gliocladium virens* GV grown on different media against the damage caused by *Sclerotium rolfsii* in *Mentha arvensis* cv. Himalaya

| Bio-control agent | Medium on which derived | Crop protection and growth parameters under artifical *Sclerotium rolfsii* infection | | | | |
|---|---|---|---|---|---|---|
| | | Seedling mortality (%) | Diseases control (% relative to no bio-control treatment) | Plant height (cm) | Number of branches per plant | Herb yield (g/pot) | Oil content (%) |
| No bio-control agent | — | 66.2 | — | 44.6 | 4.6 | 46.8 | 0.59 |
| *Gliocladium viride* | *Cymbopogon winterianus* | 9.3 | 86 | 60.0 | 11.0 | 100.2 | 0.70 |
| | Sorghum grains | 10.6 | 84 | 59.0 | 11.2 | 94.6 | 0.78 |
| *Trichoderma harzianum* | *C. winterianus* | 7.4 | 89 | 64.0 | 13.0 | 98.6 | 0.82 |
| | Sorghum grains | 11.3 | 83 | 63.0 | 13.6 | 91.4 | 0.80 |

TABLE 3

Survival of *Trichoderma harzianum* TH and *Gliocladium virens* GV on storage of culture mass for six months

| Medium | Percent surviving colony forming units (cfu) in the culture mass stored for six months | |
|---|---|---|
| | *Trichoderma harzianum* | *Gliocladium viride* |
| Wheat bran | 10.5 | 3.7 |
| Sorghum grain | 12.5 | 9.1 |
| *Mentha arvensis* distilled herbage | 38.4 | 14.0 |
| *Cymbopogon winterianus* distilled herbage | 44.0 | 13.7 |

These experiments conducted by us in our laboratory clearly show-that the distilled waste of *C. winterianus* and *M. arvensis* are suitable substrates for large scale multiplication of *T. harzianum* TH and *G. virens* GV and has several advantages over conventional media like:

(a) Survival of these fungi is higher on storage of the cultures, (b) It's incorporation into soil acts as organic amendment and enhances the fertility status (Patra et al, 1997, In: Plant nutrition—for sustainable food production and environment, Kluwer Academic Publishers, Japan), (c) Cheaper way of achieving high cfu of both *T. harzianum* TH and *G. virens* GV for field application without affecting the valuable food grains for media preparation.

What is claimed is:

1. A process for the preparation of a growth media for mass multiplication of bio-control fungi, which comprises (a) shade drying of a distillation waste recovered after distillation of plant herbage, (b) chopping the shade dried distillation waste, (c) filling the distillation waste in bags, (d) plugging the bags with cotton followed by autoclaving at 15 lbs pressure for one hour and inoculation of these bags with one or more of a bio-control fungi, (e) incubation of the bags in well illuminated room at room temperature ranging between 15–34° C. for 14–30 days, and (f) shade drying of the resultant product and grinding the same in a blender to obtain a fine powder.

2. A process as claimed in claim 1 wherein the distillation waste is from an aromatic plant selected from the group consisting of *Cymbopogon winterianus, Cymbopogon martini*, Mentha sp, unused waste of poppy husk shell and musk dana fruit.

3. A process as claimed in claim 1 wherein the distillation waste is recovered from a plant selected from the group consisting of *Cymbopogon winterianus* and *mentha arvensis*.

4. A process as claimed in claim 1 wherein the filling of the wastes is carried out in polyproplyene/poly-ethylene, synthetic, semi-synthetic, or natural bags resistant to water and distillation wastes.

5. A process as claimed in claim 1 wherein the bio-control fungi is selected from the group consisting of *Trichoderma harzianum, Gliocladium virens* and *Trichoderma virens*.

* * * * *